United States Patent [19]
Igaue et al.

[11] Patent Number: 5,626,573
[45] Date of Patent: May 6, 1997

[54] PANTS TYPE DISPOSABLE DIAPER

[75] Inventors: Takamitsu Igaue; Tohru Sasaki; Hiroyuki Soga, all of Kawanoe, Japan

[73] Assignee: Uni-Charm Corporation, Ehime-ken, Japan

[21] Appl. No.: 528,458

[22] Filed: Sep. 14, 1995

[30] Foreign Application Priority Data

Sep. 20, 1994 [JP] Japan .................... 6-225290

[51] Int. Cl.$^6$ .................. A61F 13/15; A61F 13/20
[52] U.S. Cl. .................. 604/385.1; 604/389; 604/393; 24/304
[58] Field of Search ............... 604/385.1, 385.2, 604/386, 387, 389, 393, 397, 390, 394, 396; 24/304, DIG. 11

[56] References Cited

U.S. PATENT DOCUMENTS

| | | | |
|---|---|---|---|
| 2,931,747 | 4/1960 | Dexter | 604/389 |
| 3,044,467 | 7/1962 | Campau | 604/387 |
| 3,913,578 | 10/1975 | Schaar | 604/385.1 |
| 4,820,296 | 4/1989 | Masliyah | 604/385.1 |
| 5,403,302 | 4/1995 | Roessler et al. | 604/389 |
| 5,413,568 | 5/1995 | Roach et al. | 604/385.1 |

FOREIGN PATENT DOCUMENTS

| | | | |
|---|---|---|---|
| 0623330 | 11/1994 | European Pat. Off. | 604/389 |
| 5-21935 | 3/1993 | Japan . | |
| 539531 | 5/1995 | Japan . | |

*Primary Examiner*—David H. Willse
*Assistant Examiner*—Ki Yong O
*Attorney, Agent, or Firm*—Lowe, Price, LeBlanc & Becker

[57] ABSTRACT

A pants type disposable diaper having elastic ribbons around a waist-portion and a pair of leg-portions of said diaper, respectively, is provided on a transversely central zone of a crotch section on a front or rear side of said diaper, respectively, with a vertically extending fastening tape having an adhesive section provisionally bonded to the outer surface of a backsheet of said diaper and an upper end or a lower end permanently bonded to the outer surface of said backsheet.

2 Claims, 2 Drawing Sheets

PANTS TYPE DISPOSABLE DIAPER

BACKGROUND OF THE INVENTION

The present invention relates to a pants type disposable diaper and, more particularly to, a pants type disposable diaper with fastening tape for the purpose of the used diaper in rolled state.

Before disposal of a disposable diaper smeared with excretions, the diaper is often rolled up and fastened in this state utilizing an adhesive tape or a rubber band. If the diaper is of open type provided on its transversely opposite sides with adhesive tape fasteners, these fasteners can be used also as a fastening means in the place of the adhesive tape or the rubber band. For the diaper of pants type usually having none of these adhesive tape fasteners, it is well known, for example, from Japanese Laid-Open Utility Model Application Nos. 1993-21935 and 1993-39531, to previously provide the diaper with a fastening tape for the purpose of keeping the used diaper in rolled up state.

Both of the above-cited applications disclose the technique according to which the fastening tape is peelably bonded to the top- or backsheet adjacent a waist-opening or leg-openings of the diaper. However, these openings are usually provided along their peripheral edges with elastic members bonded thereto with an appropriate tension to form the gathers which may cause the fastening tape to be finely undulated. Consequently, the fastening tape may be unintentionally peeled off from the top- or backsheet, resulting in that its adhesive surface thus exposed may be contaminated and become ineffective prior to its actual use. In addition, the tip end of the fastening tape to be held between the fingers to peel off the peelably bonded tape from the top- or backsheet may be buried in the gathers and the user's time may be wastefully taken to find the tip of the tape. Furthermore, the rigidity of the tape being higher than both the rigidity of the topsheet and the rigidity of the backsheet makes no formation of gathers on the locations underlying the tape and adjacent therearound. As a result, these locations having no gathers are pronounced and makes appearance of the diaper unattractive. Even if the gathers are formed at such locations, a sharp peripheral edge of the tape may stimulate the user's skin.

Accordingly, it is a principal object of the invention to solve the various problems of the foresaid well known techniques by providing a diaper at a transversely central zone of a crotch section free from the formation of gathers due to the presence of a liquid-absorbent core having a relatively high rigidity on front or rear side of the diaper with a fastening tape adapted to be peeled off from the diaper upwardly or downwardly.

SUMMARY OF THE INVENTION

The object set forth above is achieved, according to the invention, by a pants type disposable diaper generally comprising a liquid-permeable topsheet, a liquid-impermeable backsheet, a liquid-absorbent core disposed between these two sheets, and elastic members being stretchably substantially in circumferential direction around a waist-portion and a pair of leg-portions, respectively, wherein on front or rear side of the diaper, the outer surface of the backsheet is provided at a transversely central zone of a crotch section on the side with a vertically extending fastening tape having an adhesive section provisionally bonded to the outer surface and an upper end or a lower end permanently bonded to the outer surface.

Preferably, the tape is longitudinally folded in two sections, the outer surface of the lower section is permanently bonded to the outer surface of the backsheet, the inner surface of the upper section is applied with adhesive so that the inner surface is at least partially is provisionally bonded to the inner surface of the upper section, and these two sections are permanently bonded to each other in the proximity of a line along which the tape is longitudinally folded in the two sections. Preferably, the elastic member provided around the waist comprises elastic ribbons of a relatively high contractile force bonded along a peripheral edge of a waist-opening and elastic ribbons of a relatively low contractile force bonded to at least one of front and rear bodies.

With the pants type disposable diaper constructed as has been described above, the presence of the elastic members from gathers around the waist as well as around the legs but substantially no gathers at a transversely central zone of the front or rear crotch section containing the liquid-absorbent core having a relatively high rigidity. Accordingly, the tape provided at the central zone is affected neither by the gathers formed around the waist nor by the gathers formed around the legs and never undulated as the diaper of well known art has been the case.

PREFERRED EMBODIMENTS OF THE INVENTION

Figure 1:
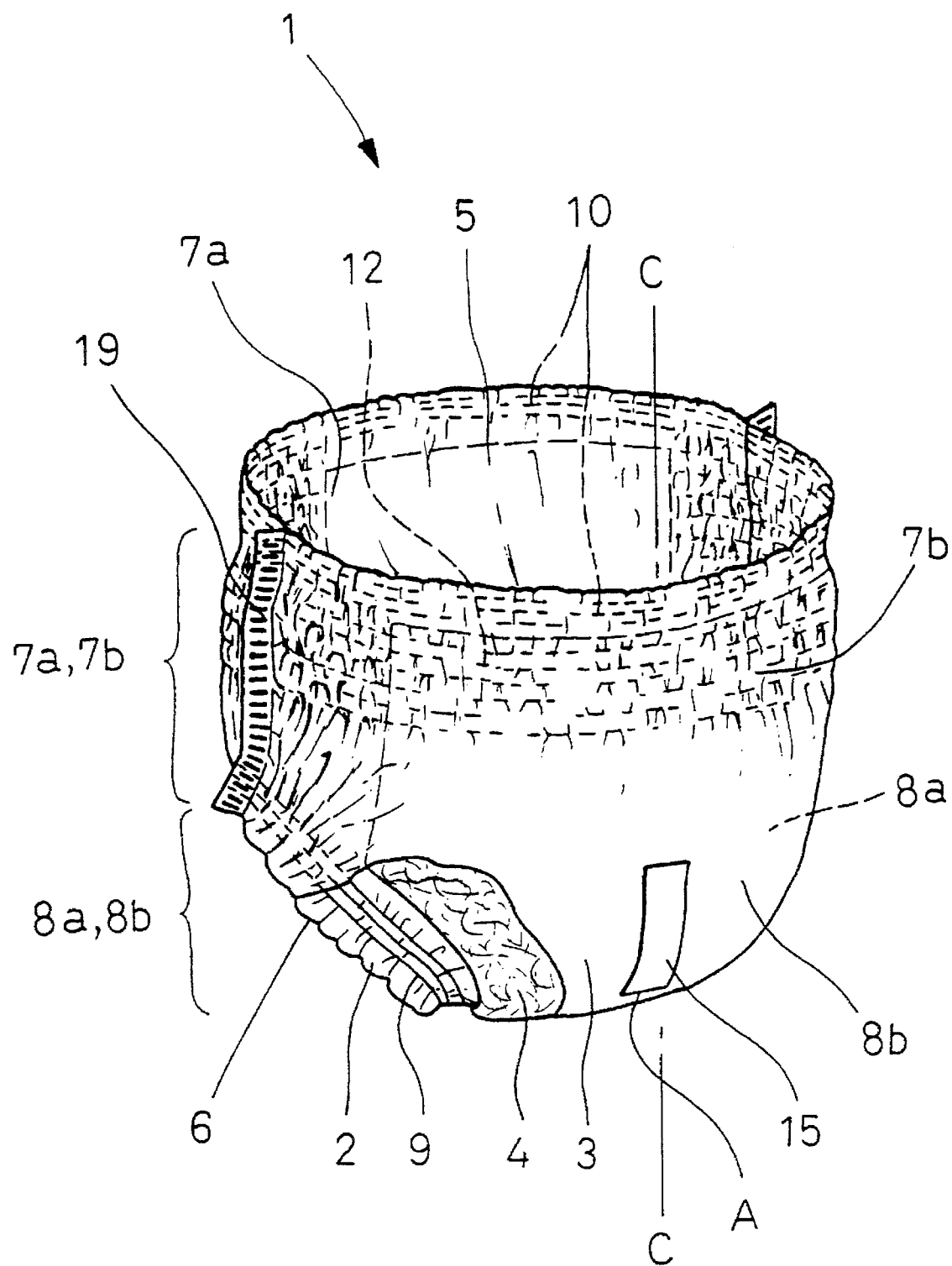
FIG. 1 is a perspective view of a pants type disposable diaper according to the invention as viewed from behind and partially broken away.

Referring to FIG. 1, a diaper 1 comprises a liquid-permeable topsheet 2 made of nonwoven fabric, a liquid-impermeable backsheet 3 made of plastic film and a liquid-absorbent core 4 disposed between these two sheets 2, 3, and these components defining a waist-opening 5 and a pair of leg-openings 6. The diaper 1 is composed of, from its top to its bottom, front and rear sections 7a, 7b and front and rear crotch sections 8a, 8b. The front and rear sections 7a, 7b are permanently bonded to each other along their transversely opposite side edges with the side edges put flat together. Along peripheral edges of the waist-opening 5 and the leg-openings 6, elastic ribbons 9, 10 are bonded with appropriate tensions to at least any one of the top- and backsheets 2, 3 on the inner surface thereof. In addition, a plurality of elastic ribbons 12 transversely extending in parallel one to another are bonded with appropriate tension to at least any one of the front and rear bodies over a range corresponding to ¼ or more of a height from the peripheral edge of the waist opening 5 to the lower ends of the crotch sections 8a, 8b. These elastic ribbons 12 serve to provide a moderate fitness of the diaper around a wearer's waist and a contractile force of the individual elastic ribbon 12 is preadjusted to be weaker than that of the elastic ribbon 10. The liquid-absorbent core 4 is formed by compressing fluff pulp or a mixture of fluff pulp and highly water absorptive polymer powders and has a thickness of 3 to 20 nm. Of the members constituting the diaper 1, the liquid-absorbent core 4 has a relatively high rigidity and substantially resists a deformation even under the contractile forces of the elastic ribbons 9, 10, 12. Transversely opposite side edges of such core 4 lie adjacent the respective elastic ribbons 9 in the crotch sections 8a, 8b, and are slightly spaced from the respective bonding lines 19 toward a center line C—C of the diaper 1 in the front and rear sections 7a, 7b. On the backside of the diaper 1, the crotch section 8b is provided with a fastening tape 15 vertically extending on the center line C—C. When the diaper 1 is in a state being free from any restraint, the elastic ribbons 9, 10, 12 contract so as to form a plurality of gathers in the proximity of the respective openings 5, 6 as well as in the front and rear sections 7a, 7b, but the crotch sections 8a, 8b fully occupied by the core 4 of a high rigidity present substantially no gathers, so the section of the backsheet 3 defined by these crotch sections 7a, 7b is smooth.

Figure 2:
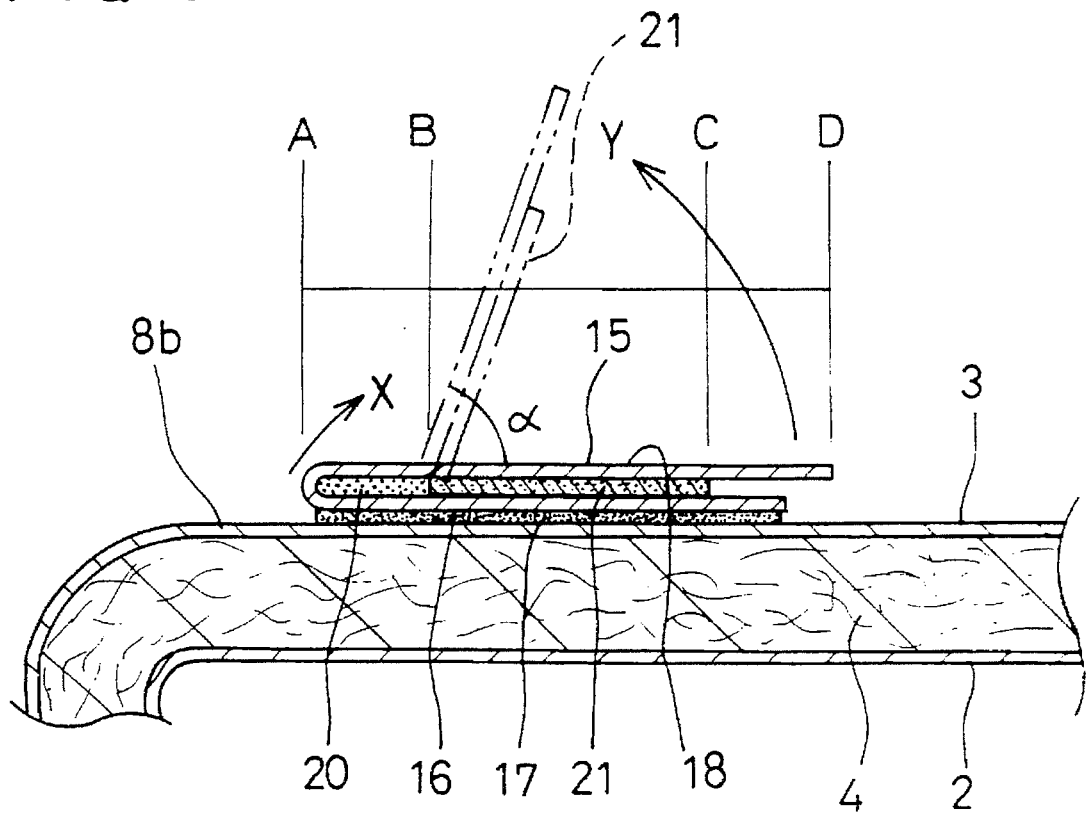
FIG. 2 is a sectional view taken along a line C—C in FIG. 1, showing an important part of the diaper.

Referring to FIG. 2, the fastening tape 15 comprises a base strip made of plastic film or nonwoven fabric and having a width of 5 to 30 mm. Such base strip is longitudinally folded back on itself along a fold line "A" into two sections with the fold line "A" lying adjacent the lower end of the crotch section 8b. The lower section 16 of the folded base tape has a length of 10 to 60 mm and bonded to the outer surface of the backsheet 3 by an adhesive layer 17 in a manner that the section 16 cannot be easily peeled off from the backsheet 3. A dimension of an upper section 18 defined between "A" and "D" as shown is longer than the lower section 16. The upper section 18 carries an adhesive layer 20 along its subsection of 3 to 10 mm defined between "A" and "B" and the subsection "AB" is permanently bonded to the inner surface of the lower section 16. The upper section 18 also carries an adhesive layer 21 along its subsection of 10 to 60 mm defined between "B" and "C" and the subsection "BC" is provisionally bonded to the inner surface of the lower section 16. The upper section 18 carries no adhesive layer along a subsection of 5 to 20 mm defined between "C" and "D" and the subsection "CD" serves as a grip. The tape 15 may be pulled with the grip "CD" held between the fingers in the direction as indicated by an arrow "Y", downwardly of the diaper 1 to peel the upper section 18 off from the lower section 16 along the subsection "BC" and thereby to expose the adhesive layer 21. Adhesive strength of the layers 17 and 20 is preadjusted to be substantially higher than that of the layer 21 so that the upper section 18 of the tape 15 can be peeled off from the lower section 16 until the position "B" but not further beyond this position "B" toward the position "A".

Figure 3:
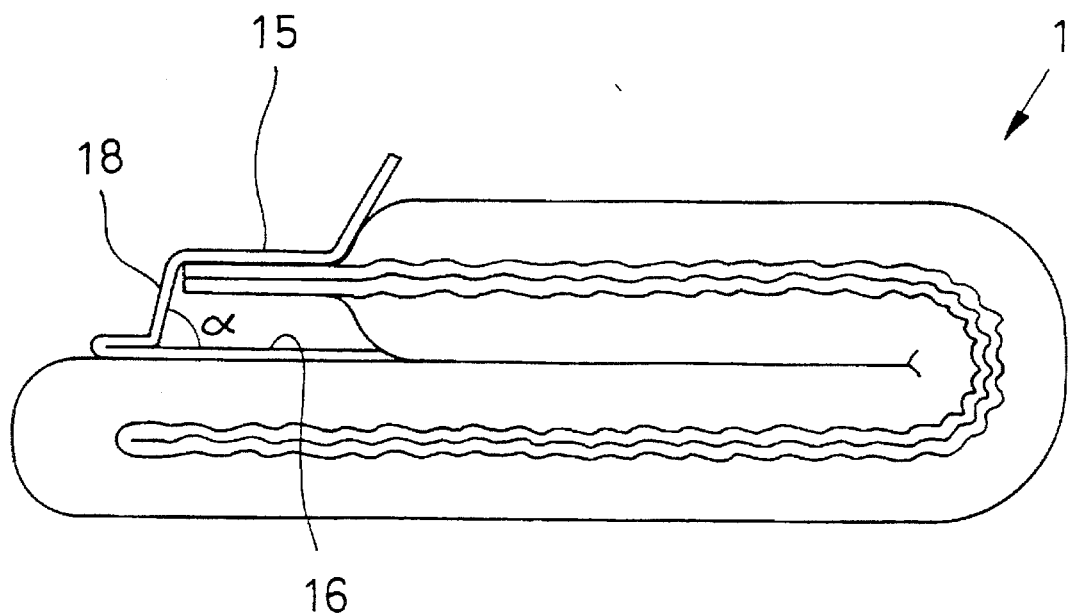
FIG. 3 is a schematic side view of the diaper as being folded in two and fastened in this state.

Referring to FIG. 3, the section of the diaper 1 which has been folded back may be fastened by the subsection "BC" of the tape 15 carrying thereon the layer of adhesive serving for provisional bonding to prevent the diaper 1 from being unfolded. Fastening the used diaper 1 in its folded state may sometimes cause the upper section of the tape 15 to be spaced from the inner surface of the lower section 16 by an angle α of 90° or larger around the boundary line "B" of the layers 20, 21 of adhesive and, in this case, the layer 20 of adhesive may be subjected along the boundary line "B" to a high force tending to peel the layer 20 of adhesive off from the inner surface of the lower section 16. Nevertheless, the subsection "AB" is never peeled off therefrom, since the layer 20 of adhesive has an adhesion sufficient to resist such peeling off. Since the subsection "AB" thus functions to suppress a force which might peel the tape 15 in the direction as indicated by an arrow "X" off from the backsheet 3 on the fold line "A" defining the boundary line of the tape 15 and the backsheet 3, an apprehension that the tape 15 might be peeled off from the diaper I is avoided even if the layer 17 of adhesive is relatively low adhesive strength.

With the diaper 1 of the invention, bonding between different members as well as between different portions of the same members may be achieved by using adhesive of various types or the heat-sealing technique, except for the section "BC" of the tape 15. While the tape 15 is shown and described as it is adapted to be partially peeled off from the diaper downwardly of the diaper and attached to the diaper on the backside thereof, an alternative arrangement is also possible without departing from the scope of the invention that the tape 15 is adapted to be partially peeled off from the diaper upwardly of the diaper and attached to the diaper on the front side thereof. An alternative arrangement is also possible that the tape 15 comprises a single strip of base tape having one end permanently bonded to the diaper and the remainder provisionally bonded thereto, instead of folding this single strip of base tape in two sections. The backsheet 3 may be also made of stretchable plastic film or plastic film having its outer surface laminated with nonwoven fabric to provide a cloth-like touch. In the latter case, the adhesive tape 15 may be attached to the outer surface of the nonwoven fabric.

Even if the diaper is designed to have gathers, the pants type disposable diaper according to the invention solves the problems of the conventional diaper of the similar type such that the fastening tape might be affected by the gathers to be unintentionally peeled off from the diaper before its actual use and/or the grip end of the tape to be held between the fingers when the diaper is actually used might be buried in the gathers. Particularly by attaching the tape to the diaper on the backside, it is possible to avoid an apprehension that the tape might be peeled off from the diaper with a result that its adhesive surface might be smeared and become ineffective even if a baby intends to play with the tape. A trouble that the tape might be entirely peeled off from the diaper is reliably avoided by folding the strip of base tape in upper and lower sections and permanently bonding the lower section to the diaper.

What is claimed is:

1. A disposable pants, comprising:
   a liquid-permeable topsheet;
   a liquid-impermeable backsheet;
   a liquid-absorbent core disposed between said topsheet and said backsheet;
   said topsheet, backsheet and core establishing a front section, a rear section and a crotch section therebetween of said pants;
   first and second elastic members provided around waist portions and leg-portions, respectively, formed in said front, rear and crotch sections; and
   a discard fastening tape extending longitudinally of said backsheet at said crotch section on an outer surface of said backsheet, said fastening tape being folded into upper and lower longitudinally extending sections, an outer surface of said lower section being attached to the outer surface of said backsheet, an inner surface of said upper section being applied with a first adhesive so that said inner surface is releasably bonded to an inner surface of said lower section; and
   wherein said upper and lower sections are bonded to each other with a second adhesive having an adhesive strength higher than that of the first adhesive, said second adhesive being disposed directly adjacent a fold line along which said tape is folded longitudinally thereof into said upper and lower sections.

2. The disposable pants according to claim 1, wherein said first elastic member comprises first elastic ribbons of a relatively high contractile force bonded along a peripheral edge of the waist portions and second elastic ribbons of a relatively low contractile force bonded to at least one of said front and rear sections.

* * * * *